US00PP16635P3

(12) United States Plant Patent
Danziger

(10) Patent No.: US PP16,635 P3
(45) Date of Patent: Jun. 13, 2006

(54) ***CHRYSANTHEMUM* PLANT NAMED 'DANCHRYATPINK'**

(50) Latin Name: *Chrysanthemum morifolium*
Varietal Denomination: Danchryatpink

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 91 days.

(21) Appl. No.: 10/825,115

(22) Filed: Apr. 16, 2004

(65) Prior Publication Data

US 2005/0283878 P1 Dec. 22, 2005

(51) Int. Cl.
*A01H 5/00* (2006.01)

(52) U.S. Cl. ..... Plt./286

(58) Field of Classification Search ..... Plt./286, Plt./297

See application file for complete search history.

*Primary Examiner*—Kent Bell
(74) *Attorney, Agent, or Firm*—Foley & Lardner LLP

(57) ABSTRACT

A new and distinct *Chrysanthemum* plant named 'Danchryatpink' characterized by having oblong shaped light violet ray florets RHS 84C; flowering time—7.5 weeks; short day plant; and vigorous growth habit.

2 Drawing Sheets

Genus and species of the plant claimed: *Chrysanthemum morifolium.*
Variety denomination: 'Danchryatpink'.

BACKGROUND OF THE INVENTION

The present invention relates to a new and distinct cultivar of *Chrysanthemum* plant, botanically known as *Chrysanthemum morifolium,* hereinafter referred to by the cultivar name 'Danchryatpink'.

The new cultivar 'Danchryatpink' originated as a natural occurring whole plant mutation of the *Chrysanthemum* cultivar 'Danchryat' in Moshav Mishmar Hashiva, Israel. The parental cultivar 'Danchryat' (patented, U.S. Plant Pat. No. 15,045). The new cultivar 'Danchryatpink' was discovered and selected by the inventor, Gabriel Danziger, as a single flowering plant growing among plants of 'Danchryat' in September, 2001, in Moshav Mishmar Hashiva, Israel.

'Danchryatpink' was selected in a cultivated environment in Moshav Mishmar Hashiva, Israel. Asexual reproduction of the new cultivar by stem cutting was first performed in January, 2002, in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be basic characteristics of 'Danchryatpink' which in combination distinguish this *Chrysanthemum* as a new and distinct cultivar:

1. Oblong shaped, light violet ray florets RHS 84C;
2. Flowering time—7.5 weeks;
3. Short day plant; and
4. Vigorous growth habit.

'Danchryatpink' has not been observed under all possible environmental conditions. The phenotype of the new cultivar may vary significantly with variations in environment such as temperature, light intensity, and daylength without any change in the genotype of the plant.

Of the many commercial cultivars known to the inventor, the most similar in comparison to 'Danchryatpink' is the parental cultivar 'Danchryat'. 'Danchryatpink' differs from 'Danchryat' in flower color. 'Danchryatpink' has light violet ray florets while 'Danchryat' has white ray florets.

BRIEF DESCRIPTION OF THE DRAWINGS

The accompanying photographs illustrate the overall appearance of the new *Chrysanthemum* cultivar 'Danchryatpink' showing the colors as true as is resonably possible with colored reproductions of this type. Colors in the photographs may differ slightly from the color values cited in the detailed botanical which accurately describe the colors of 'Danchryatpink'.

The first photograph shows a side view perspective of a corymb of 'Danchryatpink'.

The second photograph shows a close-up of the flowers of 'Danchryatpink'.

DETAILED BOTANICAL DESCRIPTION

The following observations, measurements and values describe the new cultivar as grown in Moshav Mishmar Hashiva, Israel under conditions which closely approximate those generally used in commercial practice. Premium growth conditions include regular irrigation and fertilization using moderate regin; and recommended temperature range of 22° C.–23° C. 'Danchryatpink' is mainly grown in greenhouses but can also be grown outdoors during summer. Color references are made to The Royal Horticultural Society Colour chart (R.H.S.), except where general colors of ordinary significance are used. Color values were taken under daylight conditions at approximately 12:00 pm. in Moshav Mishmar Hashiva, Israel. The age of the plants described is 11 weeks from planting.

Propagation: Stem cutting.

Plant:

*General appearance and form.*—Height: 90 cm. Width: 20 cm. Shape: Compound Corymbifor. Flowering response: Short day type. Flowering season: Autumn and beginning of winter. Winter hardiness: Hardy in moderate climate. Lastingness of the individual bloom: On the stem: 3–4 weeks; Off the stem: 2–3 weeks. Rooting habit: Adventitious roots from cutting base. Time to initiate roots: 6–7 days. Fragrance: None.

Foliage:

*Overall shape of leaf.*—Pinnatipartite.

*Base shape.*—Wedge-shaped.

*Apex shape.*—Rounded.

*Margin.*—Serrate.

*Texture.*—Slightly warty.

*Leaf length.*—10 cm.

*Leaf width.*—5.5 cm.

*Color of upper surface.*—Mature leaf: Yellow-green, RHS 147-A. Immature leaf: Yellow-green, RHS 147-A.

*Color of lower surface.*—Mature leaf: Yellow-green, RHS 147-B. Immature leaf: Yellow-green, RHS 147-B.

*Venation color.*—Upper surface: Yellow-green, RHS 147-B. Lower surface: Yellow-green, RHS 147-C.

*Petiole.*—Length: 2 cm. Diameter: 4 mm. Color: Yellow-green, RHS 146-A.

Inflorescence:

*Flowering response.*—Short day.

*Quantity of inflorescences on average.*—7–8 on average per stem.

*Inflorescence bud.*—Height: 1 cm. Diameter: 16 mm. Color: Yellow-green, RHS 146-B.

*Inflorescence size.*—Diameter: 9.5 cm. Depth (height): 18–20 mm. Diameter of disc: 18 mm.

*Ray florets.*—Shape: Oblong. Length: 35–40 mm. Width: 12–13 mm. Apex: 6–8 mm. Margin: Entire. Texture: Smooth. Number of ray florets per inflorescence: 30–32. Color when opening: Light violet, RHS 84C. Color when fully opened upper surface: Light violet, RHS 84C. Color when fully opened lower surface: Pale violet, RHS 84D.

*Disc florets.*—Shape: Bell shaped (campanulate). Length: 4–5 mm. Width: 1 mm. Apex: Serrated. Margin: Entire. Texture: Smooth. Number of disc florets per inflorescence: 200–220. Color when opening: Yellow-green, RHS 146-B. Color when fully opened upper surface: Yellow, RHS 9-A. Color when fully opened lower surface: Yellow, RHS 9-C.

*Stem.*—Average length: 85–90 cm. Average diameter: 8–10 mm. Color: Yellow-green, RHS 146-B. Internode length: 15–20 mm.

*Phyllaries.*—Number: Typical: 15–18; Observed: 18. Length: Typical: 6–9 mm; Obvserved: 7 mm. Width: Typical: 1–2 mm; Observed: 2 mm. Overall shape: Oblong. Apex shape: Rounded (Obtuse). Base shape: Truncate. Margin: Entire. Color: Upper surface: Yellow-green, RHS 148-B. Lower surface: Yellow-green, RHS 144-A.

*Peduncles.*—Length: 15 cm. Diameter: 3.5–4 mm. Texture: Slightly warty. Color: Yellow-green, RHS 146-B.

Reproductive organs:

*Androecium.*—Present in disc florets only. Stamen: Number: 5 fused as a tube. Color: Yellow, RHS 13-A. Anthers: Color: Yellow, RHS 13-A. Pollen: Color: Yellow, RHS 13-A.

*Gynoecium.*—Present in both ray and disc florets. Stigma: Color: Yellow, RHS 12-B. Ovary: Color: Yellow-green, RHS 149-D.

*Seeds.*—Width: 0.8–1 mm. Length: 1.5 mm. Shape: Oblong. Color: Grayed-green, RHS 197-A.

*Fruit.*—Achene. Color: Grayed-green, RHS 197-A.

Disease resistance: Unknown. No susceptibility was observed under regular growing condition.

I claim:

1. A new and distinct *Chrysanthemum* plant named 'Danchryatpink', as illustrated and described herein.

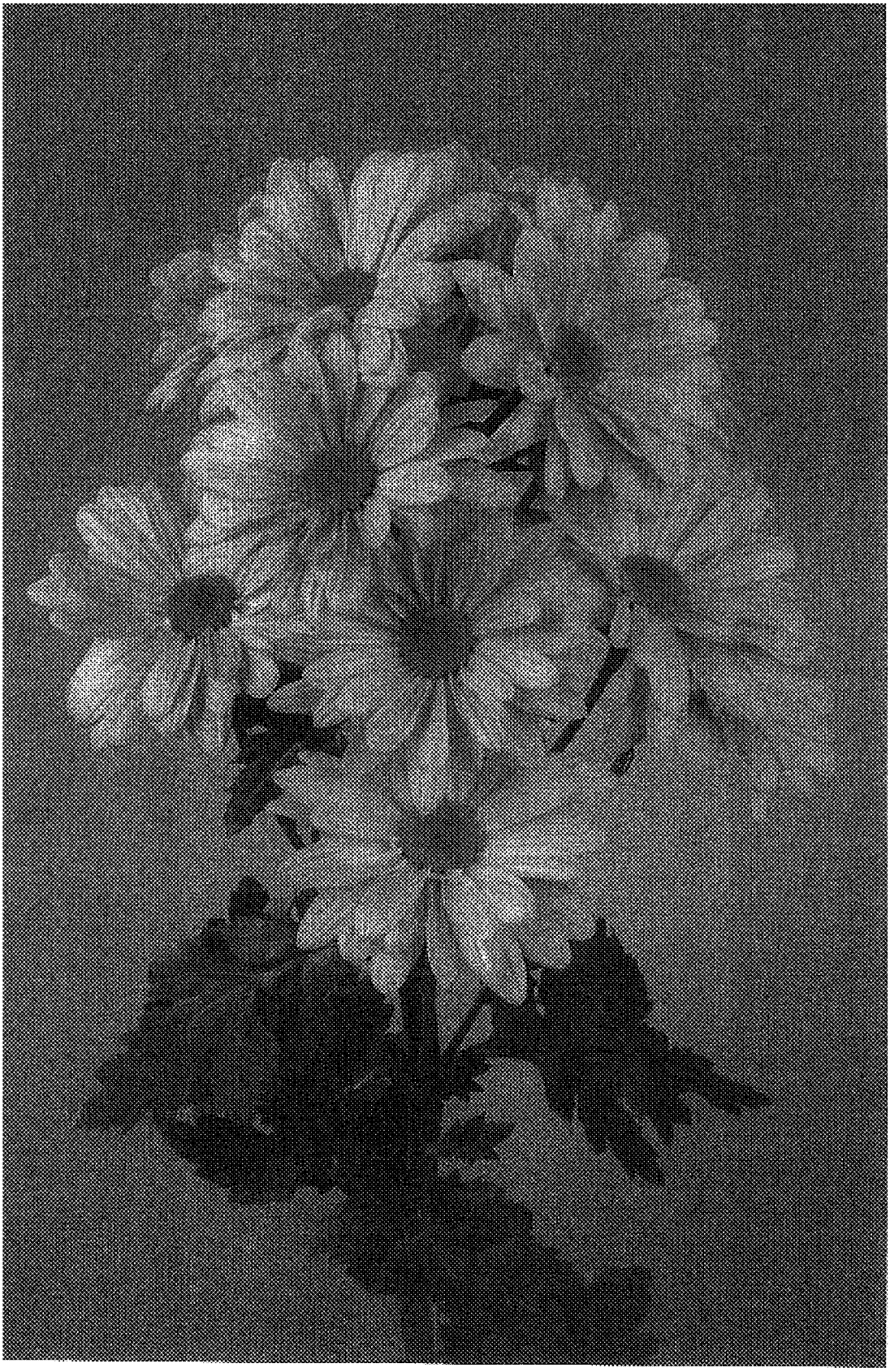

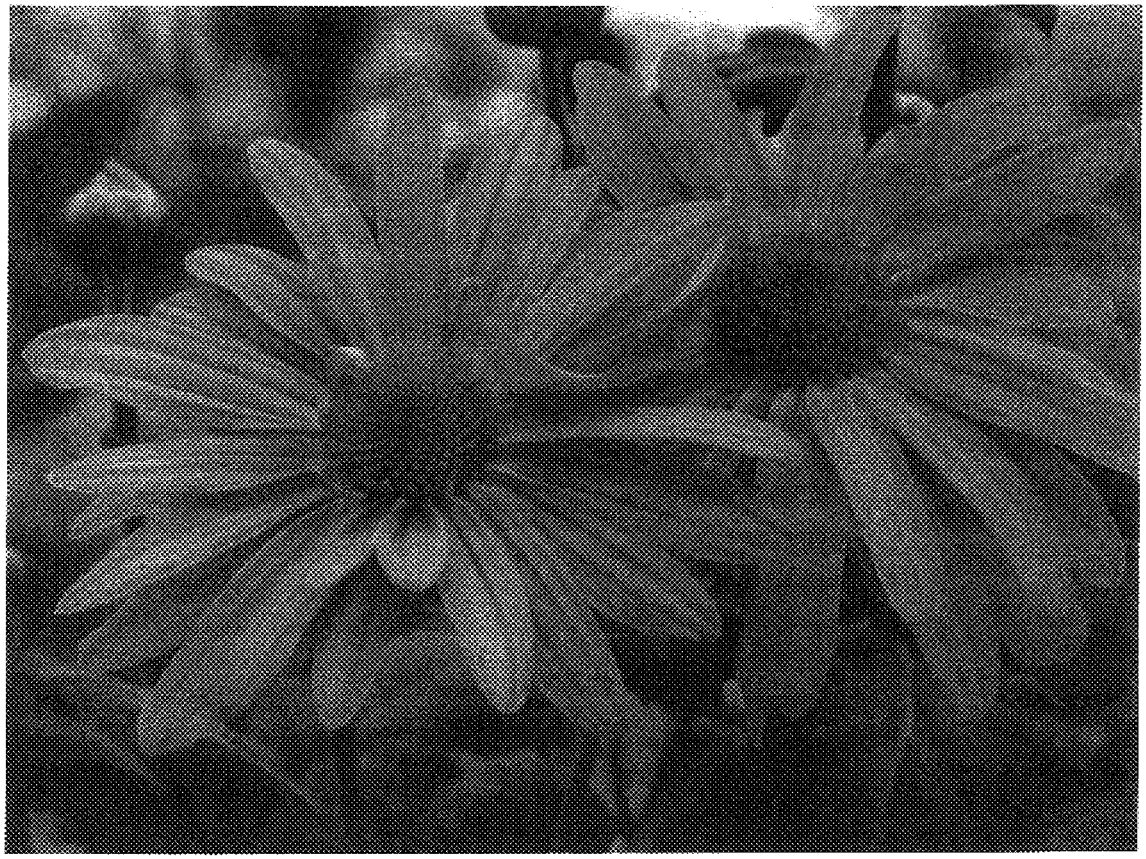

* * * * *